(12) United States Patent
Weber

(10) Patent No.: US 7,918,883 B2
(45) Date of Patent: Apr. 5, 2011

(54) NON-INVASIVE HEATING OF IMPLANTED VASCULAR TREATMENT DEVICE

(75) Inventor: Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2034 days.

(21) Appl. No.: 10/084,857

(22) Filed: Feb. 25, 2002

(65) Prior Publication Data

US 2003/0163187 A1    Aug. 28, 2003

(51) Int. Cl.
*A61F 2/06* (2006.01)
*A61M 37/00* (2006.01)

(52) U.S. Cl. .................. 623/1.15; 606/195; 606/108

(58) Field of Classification Search .............. 623/1.11, 623/1.12, 1.13, 1.14, 1.15; 606/108, 194, 606/195
See application file for complete search history.

(56) References Cited

U.S. PATENT DOCUMENTS

| | | | |
|---|---|---|---|
| 5,360,440 A | 11/1994 | Andersen | 607/116 |
| 5,545,210 A | 8/1996 | Hess et al. | 623/1 |
| 5,599,352 A | 2/1997 | Dinh et al. | 623/1 |
| 5,670,161 A | 9/1997 | Healy et al. | 424/426 |
| 5,733,327 A | 3/1998 | Igaki et al. | 623/1 |
| 5,775,338 A | 7/1998 | Hastings | 128/898 |
| 5,911,926 A | 6/1999 | Harada et al. | 264/41 |
| 5,951,881 A | 9/1999 | Rogers et al. | 216/41 |
| 5,954,744 A | 9/1999 | Phan et al. | 606/198 |
| 6,056,844 A * | 5/2000 | Guiles et al. | 156/272.4 |
| 6,149,576 A | 11/2000 | Gray et al. | 600/9 |
| 6,228,109 B1 | 5/2001 | Tu et al. | 607/113 |
| 6,231,600 B1 | 5/2001 | Zhong | 623/1.42 |
| 6,238,421 B1 | 5/2001 | Gunther et al. | 607/13 |
| 6,248,129 B1 | 6/2001 | Froix | 623/1.42 |
| 6,253,443 B1 | 7/2001 | Johnson | 29/557 |
| 6,364,823 B1 * | 4/2002 | Garibaldi et al. | 600/12 |
| 6,786,904 B2 * | 9/2004 | Doscher et al. | 606/28 |

FOREIGN PATENT DOCUMENTS

WO    WO 00/45868    2/1999
WO    WO 00/66192    4/2000

OTHER PUBLICATIONS

Written Opinion.

* cited by examiner

*Primary Examiner* — Vy Q Bui
(74) *Attorney, Agent, or Firm* — Brooks, Cameron & Huebsch, PLLC

(57) ABSTRACT

One embodiment of the present invention involves employing, in a vascular treatment device, a material which has a magnetic susceptibility which is heat sensitive. The vascular treatment device can then be heated remotely and non-invasively using an applied magnetic field, to a preselected temperature at which the vascular treatment device becomes substantially non-magnetically susceptible.

39 Claims, 5 Drawing Sheets

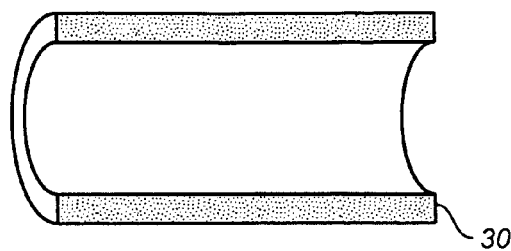
FIG._5
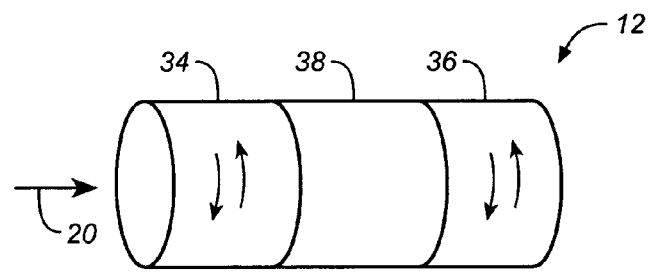
FIG._6
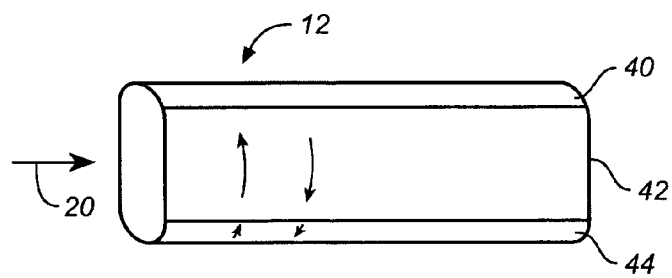
FIG._7
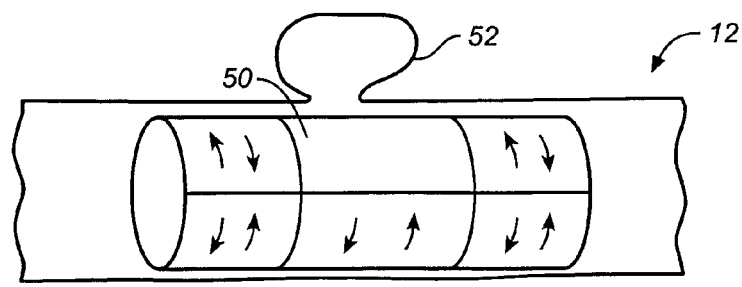
FIG._8

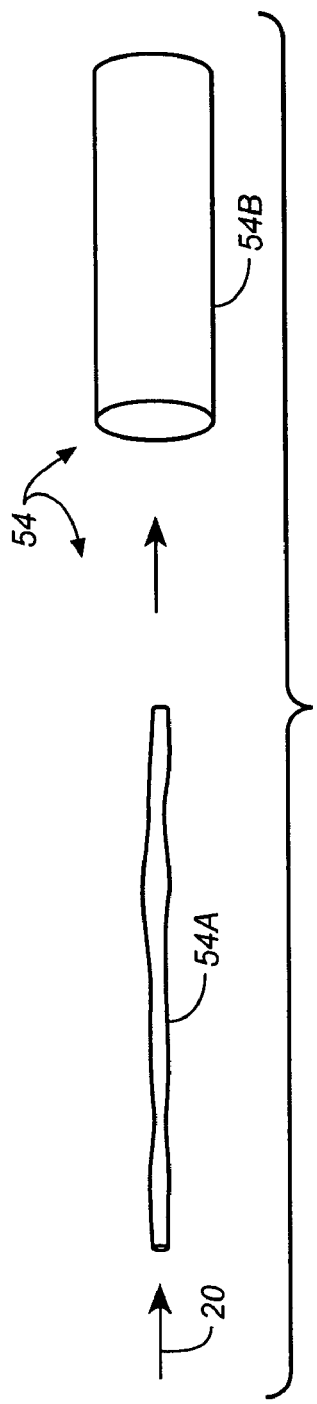
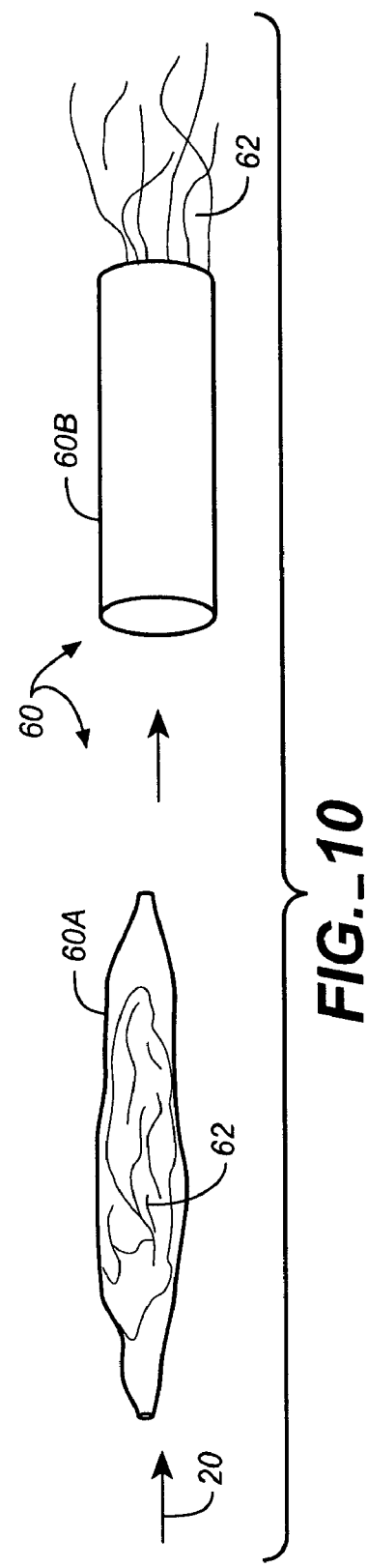

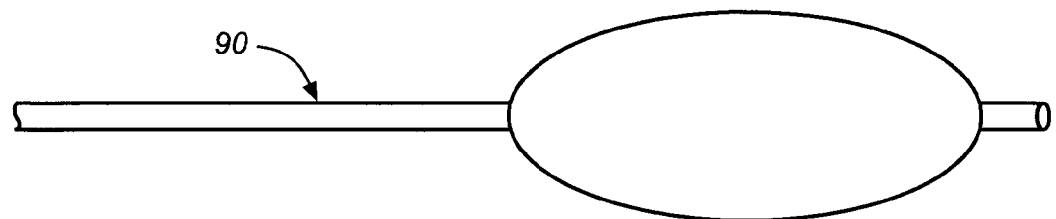
FIG._12A
FIG._12B
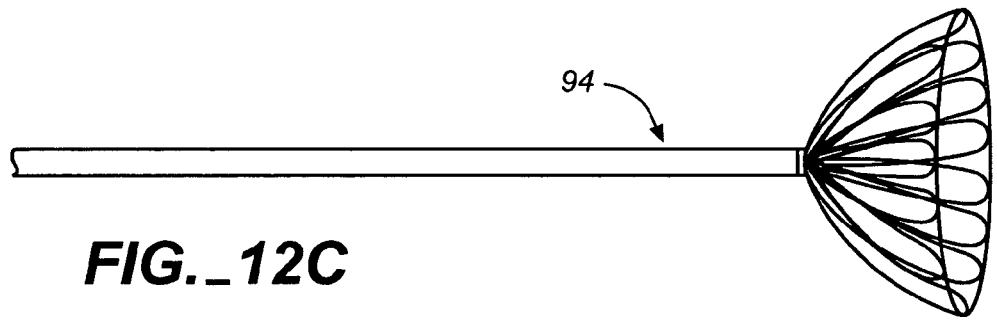
FIG._12C

NON-INVASIVE HEATING OF IMPLANTED VASCULAR TREATMENT DEVICE

BACKGROUND OF THE INVENTION

The present invention relates to heating of implanted devices. More specifically, the present invention relates to non-invasive heating of implanted vascular treatment devices, such as stents.

Current vascular treatment devices, such as stents, suffer from a number of disadvantages. Among the primary disadvantages is restenosis. A number of different methods have been proposed to address this complication. Among those methods include heating the cells proximate the stent to induce cell apoptosis.

The methods used to heat the cells vary. However, one method is described in Diamantopolous, Langenhove, Foley, Feyter, *Non-Invasive Heating of Implanted Arterial Stents In Vivo: A Novel New Method To Prevent Restenosis, Feasibility and Safety*. The method of heating the stent proposed by Diamantopolous et al. is based on inherent properties of metals when placed inside an alternating electromagnetic field. Because of the retentively of the metallic stent used in Diamantopolous et al., the stent forms a magnetic circuit. As the magnetizing force of an alternating magnetic field periodically changes, the magnetic flux inside the stent lags, resulting in power loss in the stent. At least a portion of the power loss, of course, manifests itself as heat.

In Diamantopoulos et al., a high frequency alternating magnetic field was generated based on control signals from a personal computer. In a human coronary artery model, donor blood was pressurized to achieve a desired flow rate through the model. The stents were heated to 60° C. Diamantopoulos et al. also mentioned that maintenance of the stent temperature at levels of 43-45° C. would be feasible by power-algorithm and magnetic feedback techniques. Diamantopoulos et al. also verified that Nitinol stents could be heated to accomplish remote expansion.

One of the primary disadvantages with the technique mentioned by Diamantopoulos et al. is that the heating in the stent is dependent upon the change of magnetic flux through the stent. This, in turn, is dependent on the alignment and positioning of the stent relative to the magnetic field lines generated in the applied magnetic field. If the magnetic field and the stent are not aligned properly, then little or no heating effect will be obtained.

Another disadvantage with the Diamantopoulos et al. technique is that the stent temperature is raised by the resistance to the electric currents induced by the change in magnetic flux. That temperature rise is therefore not distributed homogeneously throughout the stent. This is because the stent is not a homogeneous tube, and therefore some points within the stent will become hotspots, which can damage the arterial wall.

A further disadvantage of the Diamantopoulos et al. technique is its lack of flexibility. In other words, if the stent is aligned with the magnetic field, the entire stent will heat. If it is not aligned with the magnetic field, then the stent will not heat. In either case, there is no mechanism by which only portions of the stent can be heated while retaining other portions of the stent substantially unheated under the influence of the applied magnetic field.

SUMMARY OF THE INVENTION

One embodiment of the present invention involves employing, in a vascular treatment device, a material which has a magnetic susceptibility which is heat sensitive. The vascular treatment device can then be heated using an applied alternating magnetic field to the temperature at which the vascular treatment device becomes substantially non-magnetically susceptible.

In another embodiment, a vascular treatment device is employed which includes material that heats in the presence of an applied alternating magnetic field regardless of the orientation of the vascular device relative to the applied magnetic field. The vascular treatment device can then be heated without the need for exact alignment of the vascular treatment device (or the patient) with respect to the applied magnetic field.

In still another embodiment, an implantable vascular treatment device is formed such that only portions of it heat in the presence of an applied alternating magnetic field.

The present invention can also be implemented as methods. In one embodiment, the above heating techniques are used to heat a stent to inhibit restenosis. In still other embodiments, the above heating techniques can be used to heat and thus deploy a device, such as an expandable stent. In still other embodiments, the heating techniques can be used to remotely release therapeutic agents.

BRIEF DESCRIPTION OF THE DRAWINGS

FIG. 5 is a cross-sectional view illustrating a stent incorporating material in accordance with the present invention.

FIGS. 6-8 illustrate stents which have portions thereof heatable.

FIG. 9 illustrates the remote deployment of an expandable stent in accordance with one embodiment of the present invention.

FIG. 10 illustrates the remote release of therapeutic agent in accordance with one embodiment of the present invention.

FIGS. 11A-12C illustrate additional embodiments of the present invention.

DETAILED DESCRIPTION OF THE ILLUSTRATIVE EMBODIMENTS

Figure 1:
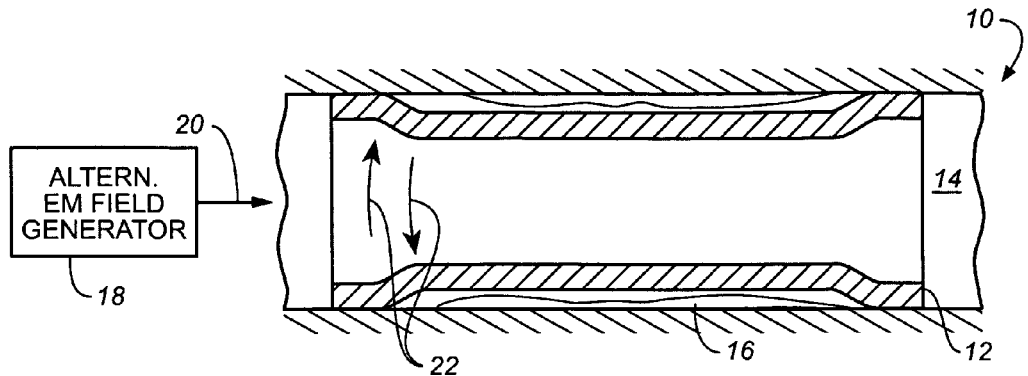
FIG. 1 is a side sectional view illustrating a stent deployed in a vessel.

FIG. 1 illustrates a system 10 for inducing heating of an intravascular treatment device. In the embodiment illustrated in FIG. 1, intravascular treatment device 12 is comprised of a stent deployed within a vessel 14 at the site of a lesion 16. FIG. 1 also illustrates alternating electromagnetic field generator 18 which generates and applies an alternating electromagnetic field from a remote location (such as external to the patient). The alternating electromagnetic field is illustrated by arrow 20 in FIG. 1.

If stent 12 is formed with, or includes, magnetically susceptible material, the alternating electromagnetic field causes current to flow in the stent material in the alternating directions illustrated by arrows 22. This causes twisting of dipoles in the stent material and thus creates heat. However, as mentioned in the background portion of the present specification, simply employing a magnetically susceptible material can result in a number of disadvantages.

Thus, in accordance with one embodiment of the present invention, stent 12 includes a magnetically susceptible material (or radio frequency (RF) acceptor material) which exhibits ferromagnetic properties in that it loses its magnetic properties when it is raised past a certain temperature referred to as the Curie point. In one illustrative embodiment, the particular material is chosen to have a Curie point within a specific, preselected, degree range such that the material will not heat above a maximum desired temperature in the presence of an alternating magnetic field. One such material is referred to as Ferrite Oxide (FEO) which is sold under the commercial designation SMART BOND by Triton Systems, Inc. of Chelmsford, Mass. and is described in U.S. Pat. No. 6,056,844.

During the Material Research Society Fall 2001 meeting, a presentation by Z. H. Zhong of the Institute for Micromanufacturing in Korea, showed a way to produce nano-sized particles (in the order of 20-100 nm) of $Cr(x)O(y)$ or $Fe(x)O(y)$. A target of Cr or Fe was placed inside a furnace flushed by Argon gas. The Argon gas stream was guided downstream to a so-called "cold-finger" a glass plate kept at low temperatures. The target was hit by a laser to induce atoms to come to the surface. Furthermore, a small gas stream of Oxygen was added to the gas flow to react with the atoms floating in the gas stream. On the cold-finger a formation of $Fe(x)O(y)$ or $Cr(x)O(y)$ nanoparticles was obtained where the x/y ratio could be adjusted by changing the oxygen flowrate. The different phases of the Ferrite or Chromium oxide posses different Curie temperatures, however, the combined nanocrystal showed a single Curie temperature adjustable between levels by changing the oxygen flow.

The use of nanoparticles in the scope of this disclosure is of benefit as it allows a much finer distribution throughout the medical device and by such a more homogeneous heat distribution. The particles of Smartbond are in the range of 500 nm or larger.

This material can be obtained with a Curie point within a temperature range of approximately 3-5 degrees Kelvin. Thus, the stent will heat to the Curie temperature and no further. By choosing material having an appropriate Curie temperature, temperatures can be achieved sufficient to inhibit restenosis, but the stent does not continue to heat sufficiently to damage the wall of vessel 14. It should be noted that the specific material mentioned above is but one exemplary material and others with desired Curie temperatures can be used as well.

Figure 2:
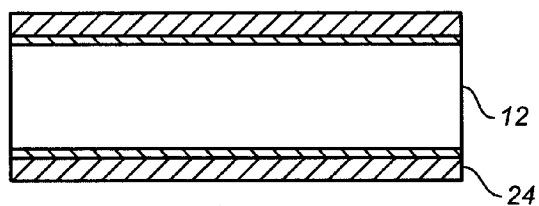
FIG. 2 is a cross-sectional view showing one embodiment of a coating on the outside of the stent shown in FIG. 1.
Figure 3:
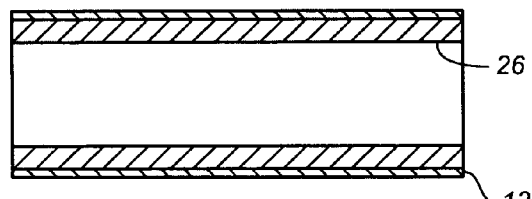
FIG. 3 is a cross-sectional view showing a coating on the inside of the stent shown in FIG. 1.
Figure 4:
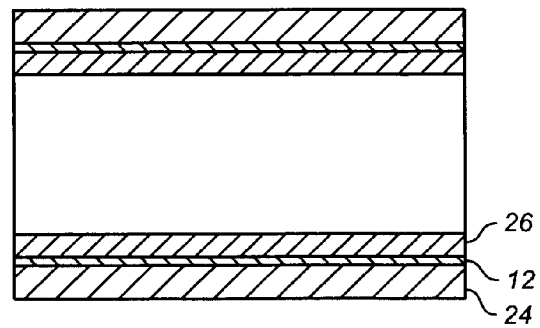
FIG. 4 is a cross-sectional view showing a stent coated on both the inside and outside.

Such materials can be applied to, or used with, vascular treatment devices (such as stents) in a wide variety of ways. For example, some such materials can be obtained in powder form and can be used to coat the stent. For example, FIG. 2 illustrates stent 12 with a coating of FEO (or similar material) 24 deployed on the exterior surface of stent 12. Of course, as shown in FIG. 3, stent 12 can have a coating 26 disposed on the interior surface thereof. Similarly, as shown in FIG. 4, stent 12 can be dipped coated or otherwise coated such that it includes both coatings 24 and 26 on the outer surface and inner surface of stent 12, respectively. The coating may illustratively be formed such that the FEO material is dispersed as a powder throughout a polymer coating which is added to the surface of the stent. In these embodiments, the stent core 12 can illustratively be formed of a conventional stent material, such as stainless steel or tantalum with the coatings 24 and/or 26 scintered on or painted on, or otherwise applied to, the stent core 12.

It should also be noted that, in these embodiments, if the stent core 12 is formed of a magnetically susceptible material, that material can still be used without obtaining undesirably high levels of heating. In that embodiment, the orientation of the applied electromagnetic field 20 is simply randomized or rotated. Since the coatings 24 and/or 26 are formed of discrete individual elements or particles, even the random or rotating magnetic field will cause heating on the coatings. However, since the electromagnetic field is randomized or rotating, it will not be properly aligned with the core stent material 12 sufficiently to obtain any undesirable heating. Thus, the stent core 12 can be formed of conventional materials even in accordance with the present invention.

It should be further noted that, of course, the entire stent 12 can be formed of the FEO (or similar material) which has the desired magnetic susceptibility properties. In addition, if the stent is formed of a polymer material, the FEO (or similar material) can be embedded in the material. Such an embodiment is illustrated by stent 30 in FIG. 5 in which stent 30 is formed of a polymer material having the desired FEO material embedded therein. Of course, even if the stent is formed of a polymer material, the FEO material can be coated thereon in a similar fashion to that shown in FIGS. 2-4.

It should also be noted that since the material forming layers 24 and 26 accepts RF fields much more readily than a conventional metal stent core, the applied electromagnetic field can simply be applied at a frequency chosen to increase the heating affect of the coatings while reducing the heating affect of the stent core. For example, the electromagnetic field can be applied at a much lower frequency than that required to undesirably heat the metal stent core 12. In that embodiment, only the portions containing the desired material in layers 24 and 26 would heat, while the metal stent core 12 would not heat undesirably.

Similarly, the present invention can be practiced using yet another technique to prevent the sent core 12 from heating. Even if stent core 12 is magnetically susceptible, and even if the electromagnetic field is applied at a frequency that would otherwise induce significant heating in stent core 12 and is not rotated or randomized, the present invention can be utilized by aligning the applied magnetic field with the patient (or stent) such that the integral of the magnetic field lines passing through the stent are substantially zero. This causes the change in magnetic flux in the stent to be zero and thus avoids heating.

> by Diamantopolous the power loss in the stent can be sensed by external sensors. Of course, when a material with a changing magnetic susceptibility is embedded in the device, this will allow a much better control of the Rf field as a sharp transition can be sensed when passing over the Curie temperature (Tc) of the embedded material. Moreover, when multiple grades of magnetic susceptible material are embedded, one can easily sense multiple temperatures.

FIGS. 6-8 illustrate yet other alternative embodiments in accordance with the present invention. It may be desirable that only certain portions of the vascular treatment device (e.g., stent 12) heat while the other portions do not heat. For example, if restenosis is more often seen at the edges of the implanted stent, or at the center, then it may be desirable that those portions be formed such that they preferentially heat relative to the other portions of the stent under the applied electromagnetic field. Similarly, if, for example, the stent is being used to bridge an aneurysm, cell growth may be highly desired in the area of the aneurysm neck. However, cell growth at the edge of the stent may not be desired. Further, in applications where the stent needs to bend during deployment, the bending portion of the stent may need to be free of coatings in order to maintain its deformability.

Thus, FIGS. 6-8 illustrate different embodiments of a stent in accordance with the present invention to address these issues. In FIG. 6, stent 12 has two opposite end portions 34 and 36 and a generally centrally located portion 38. In the embodiment shown in FIG. 6, heating is desired at the end portions 34 and 36 but not at the intermediate portion 38. This can be accomplished in a number of different ways. For example, if the stents are large enough, then the coating process can be controlled such that only ends 34 and 36 are coated with the magnetically susceptible material.

Similarly, ends 34 and 36 can be coated with additional coating material such that the heating affect is more pronounced at ends 34 and 36 than it is at intermediate portion 38. In addition, intermediate portion 38 can be formed with discontinuities therein (i.e., it can be formed with areas which are non-susceptible to the electromagnetic field). Similarly, portion 38 can be formed with areas or patches of metal which has a very high resistance, in order to inhibit currents from flowing therein. The discontinuities or application of metal with high resistance can be formed in any number of conventionally known ways. Both act as electrical discontinuities which reduce current flow and thus reduce heating in the areas where they occur. Thus, these techniques can be employed in areas of the stent where heating is not desired.

While FIG. 6 shows stent 12 divided into portions along its longitudinal axis, FIG. 7 shows stent 12 divided into portions 40, 42 and 44 about its periphery. Thus, for example, portions 42 and 44 may be formed similar to portions 34 and 36 shown in FIG. 6, while portion 40 is formed similar to portion 38. In that embodiment, portions 42 and 44 would heat to the desired temperature under the applied electromagnetic field while portion 40 would not.

FIG. 8 shows still a further embodiment in which the stent 12 is divided both along its longitudinal axis (as shown in FIG. 6) and radially (as shown in FIG. 7). This provides a stent which has a significantly larger number of portions, or patches, which can be individually selected for heating. In the embodiment shown in FIG. 8, portion 50 is adjacent a neck of an aneurysm 52 and is thus chosen such that it does not heat under the applied electromagnetic field. However, the remaining portions are chosen and configured such that they do heat. Of course, any other number of configurations with various portions heating nor non-heating can be selected as well. As but one example, the opposite of the configuration shown in FIG. 6 can be implemented. In that embodiment, the center portion 38 will be configured to heat while end portions 34 and 36 will not.

Of course, any other number of variations can be implemented as well. Similarly, the portions can be coated with different powders which have different Curie temperatures or different thicknesses or concentrations of magnetically susceptible material. Thus, the different portions of stent 12 will heat to a plurality of different temperatures. This is because they will be variously susceptible to the applied electromagnetic field or because the heating affect will be different.

FIGS. 9 and 10 illustrate two other embodiments of the present invention. In FIG. 9, the present invention is used to deploy a self-expanding stent, which expands in the presence of a temperature change. For example, FIG. 9 shows stent 54 in a collapsed position as well as in an expanded position. Stent 54 in the collapsed position is designated by the numeral 54A and stent 54 in the expanded position is designated by the numeral 54B. In one illustrative embodiment, stent 54 is formed of Nitinol material. The Nitinol is coated or otherwise has disposed thereon, the coatings discussed above. Electromagnetic field 20 is then applied to stent 54A and as it heats, it reaches the transition temperature of the Nitinol material and expands to the configuration designated 54B. The stent can thus be remotely and non-invasively expanded.

Nitinol grades with Af (Austinitic finish temperature) in the range of −25 C. to 120 C. (−13 F to 248 F.) can be obtained from Shape memory Application, Inc. of San Jose, Calif.

FIG. 10 also illustrates a stent or an expandable capsule 60 in the collapsed position illustrated by numeral 60A and in the expanded position illustrated by numeral 60B. Capsule or stent 60A includes therein a therapeutic agent 62. The therapeutic agent can be, for example, a drug, genetic material such as endothelial cells or drugs which promote the growth of endothelial cells, medicines, etc. Capsule 60A is shown in the insertion position in which the capsule is collapsed around therapeutic agent 62. The capsule 60 is then inserted to the treatment site where the therapeutic agent is to be released and electromagnetic field 20 is applied. This causes the material to heat and thus expand to the expanded position designated by numeral 60B. Expansion of capsule 60 releases the therapeutic agent 62 therefrom at the treatment site. While stent 54 and capsule 60 can be formed of Nitinol material, they can also be formed of a temperature memory polymer or other temperature sensitive material.

When different grades of magnetic susceptible material are embedded, one can trigger different therapeutic agents to be released at different times. Using the power feedback algorithm (sensing the current and voltage over the RF coil) as proposed by Diamantopolous, one can trigger only the lower Tc releasing a first drug (such as heparin), whereas in a later stage one can trigger a second drug (such as growth factor).

Figure 11A:
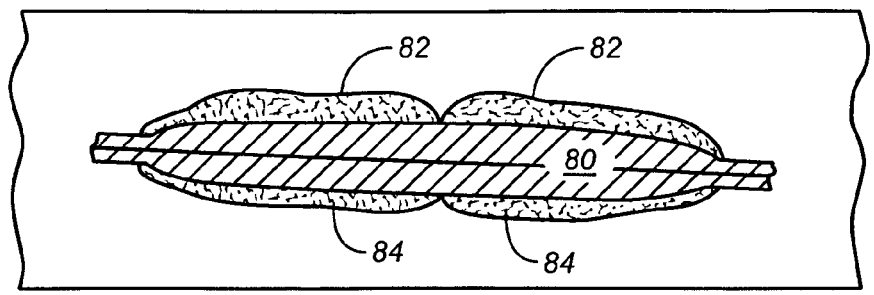
Figure 11B:
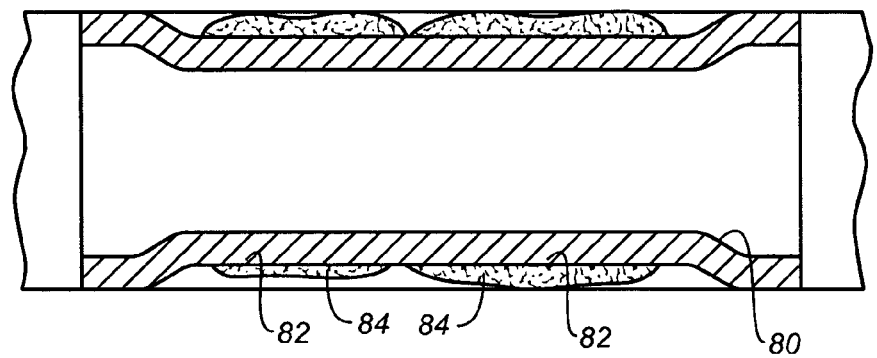
Figure 11C:
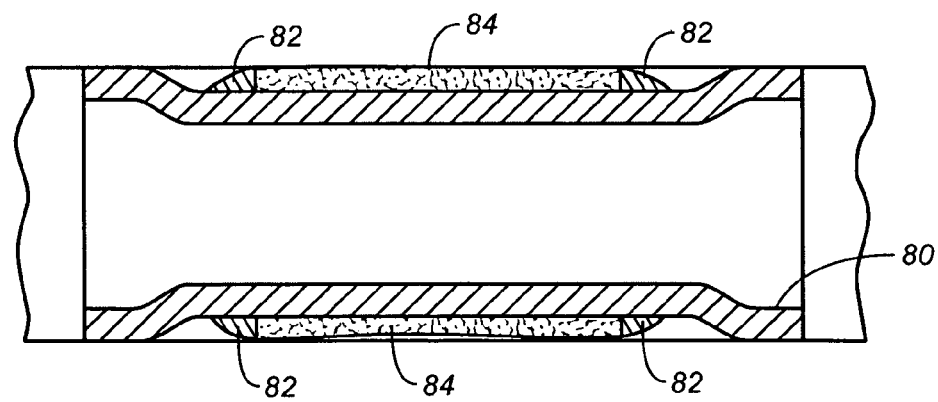

FIGS. 11A-11C illustrate yet another embodiment of the present invention. A first device (such as a shape memory alloy (SMA) stent 80) is formed with a first Curie temperature and a second capsule or set of capsules 82 (containing a therapeutic agent 84) has a second Curie temperature. FIG. 11A shows both in a collapsed position, However, when using two grades of susceptible material with two Curie temperatures Tc1 and Tc2, SMA stent 80 is heated to Tc1 to open SMA based stent 80 (which is Nitinol, for example). This is shown in FIG. 11B. Capsules 82 are then heated to Tc2 to release and activate a release of therapeutic agent 84. This is shown in FIG. 11C. When heated to Tc2, capsules 82 open and shrink back to the position shown in FIG. 11C, thus releasing therapeutic agent 84. This allows the drug or therapeutic agent 84 to be positioned on the outside of the device against the vessel wall and only to be released once the stent is firmly pressed against the wall, preventing the drug from being washed away.

It should also be noted, of course, that the present invention can be used to deploy or heat a balloon catheter 90, a filter 92, a guidewire 94, etc., as shown in FIGS. 12A-12C, respectively.

It can thus be seen that the present invention overcomes a number of significant disadvantages associated with prior art techniques. The present invention can be used to remotely and non-invasively heat stents or various portions of stents (or other vascular treatment devices) but to control heating such that it does not reach undesirable levels. The present invention can also be used to control the different portions of a stent which are heated and the temperature to which they are heated. Similarly, the present invention can be used to deploy stents or other similar vascular treatment devices. Further, the present invention can be used to release therapeutic agents at a desired treatment site in a body cavity.

Although the present invention has been described with reference to preferred embodiments, workers skilled in the art will recognize that changes may be made in form and detail without departing from the spirit and scope of the invention.

What is claimed is:

1. A vascular treatment device, comprising:
a stent formed with a magnetically susceptible material having a magnetic susceptibility that decreases within a preselected temperature range, wherein the stent includes a core, where the core is formed of the susceptible material.

2. The vascular treatment device of claim 1, wherein the susceptible material has a Curie temperature in the preselected temperature range.

3. The vascular treatment device of claim 1, wherein the stent includes a core, where the susceptible material comprises a coating on a surface of the core.

4. The vascular treatment device of claim 3, wherein the coating is disposed on an external surface of the core.

5. The vascular treatment device of claim 3, wherein the coating is disposed on an internal surface of the core.

6. The vascular treatment device of claim 3, wherein the coating is disposed on both an internal and external surface of the core.

7. The vascular treatment device of claim 3, wherein preselected portions of the core material are formed of the susceptible material and preselected portions are formed of another material.

8. The vascular treatment device of claim 3, wherein only preselected portions, less than the entire core, are coated with the susceptible material.

9. The vascular treatment device of claim 3, wherein the core comprises a magnetically susceptible material.

10. The vascular treatment device of claim 1, wherein the susceptible material comprises one of Ferrite Oxide (FEO) and Chromium Oxide (CrO).

11. The vascular treatment device of claim 10 wherein the susceptible material has a particle size less than approximately 500 nanometers.

12. The vascular treatment device of claim 1, wherein the medical device comprises:
a therapeutic agent delivery device.

13. The vascular treatment device of claim 12, wherein the delivery device includes an expandable member, self-expanding to an expanded position at a preselected temperature, and when in the expanded position the expandable member releases the therapeutic agent.

14. The vascular treatment device of claim 1, wherein the medical device comprises:
a self-expanding stent, expanding at a temperature no greater than the preselected temperature range.

15. The vascular treatment device of claim 1 wherein the medical device comprises a balloon catheter.

16. The vascular treatment device of claim 1 wherein the medical device comprises a filter.

17. The vascular treatment device of claim 1 wherein the medical device comprises a guidewire.

18. The vascular treatment device of claim 1, wherein the coating includes a polymer binder for the magnetically susceptible material.

19. The vascular treatment device of claim 1, wherein the core is a metal selected from the group stainless steel, Nitinol, and tantalum.

20. The vascular treatment device of claim 1, wherein the coating includes a sintered coating of the magnetically susceptible material on the core.

21. The vascular treatment device of claim 1, wherein the coating includes a painted coating of the magnetically susceptible material on the core.

22. A vascular treatment system, comprising:
an electromagnetic field generator; and
a medical device deliverable to a treatment site and including a magnetically susceptible material being magnetically susceptible to an electromagnetic field generated by the generator and having a Curie temperature in a preselected temperature range, such that the implantable device heats to a temperature sufficient to treat the treatment site when the electromagnetic field is applied.

23. The vascular treatment system of claim 22, wherein the medical device comprises;
a stent having a core material.

24. The vascular treatment system of claim 23, wherein the susceptible material comprises a coating on a surface of the core material.

25. The vascular treatment system of claim 24, wherein the coating is disposed on an external surface of the core material.

26. The vascular treatment system of claim 24, wherein the coating is disposed on an internal surface of the core material.

27. The vascular treatment system of claim 24, wherein the coating is disposed on both an internal and external surface of the core material.

28. The vascular treatment system of claim 24, the preselected portions of the core material are formed of the susceptible material and preselected portions are formed of another material.

29. The vascular treatment system of claim 24, wherein only preselected portions, less than the entire core, are coated with the susceptible material.

30. The vascular treatment system of claim 24, wherein the core material comprises a magnetically susceptible material.

31. The vascular treatment system of claim 23, wherein the core material is formed of the susceptible material.

32. The vascular treatment system of claim 22, wherein the susceptible material comprises one of Ferrite Oxide (FEO) and Chromium Oxide (CrO) having a particle size of less than approximately 500 nm.

33. The vascular treatment system of claim 22, wherein the medical device comprises:
a therapeutic agent delivery device.

34. The vascular treatment system of claim 33, wherein the delivery device includes an expandable member, self-expanding to an expanded position at a preselected temperature, and when in the expanded position the expandable member releases the therapeutic agent.

35. The vascular treatment system of claim 22, wherein the implantable member comprises:
a self-expending stent, expanding at a temperature no greater than the preselected temperature range.

36. The vascular treatment device of claim 22, wherein the coating includes a polymer binder for the magnetically susceptible material.

37. The vascular treatment device of claim 22, wherein the core is a metal selected from the group stainless steel, Nitinol, and tantalum.

38. The vascular treatment device of claim 22, wherein the coating includes a sintered coating of the magnetically susceptible material on the core.

39. The vascular treatment device of claim 22, wherein the coating includes a painted coating of the magnetically susceptible material on the core.

* * * * *